United States Patent [19]

Desmurs et al.

[11] Patent Number: 5,132,460
[45] Date of Patent: Jul. 21, 1992

[54] PROCESS FOR THE PREPARATION OF N-MONOALKYL OR M-MONOALKENYL ANILINES

[75] Inventors: Jean-Roger Desmurs, Communay; Hubert Kempf, Lyons; Francis Back-Posta, Craponne, all of France

[73] Assignee: Rhone-Poulenc Chimie, Cedex, France

[21] Appl. No.: 532,334

[22] Filed: Jun. 5, 1990

[30] Foreign Application Priority Data

Jun. 5, 1989 [FR] France .................... 89 07388

[51] Int. Cl.⁵ .......................... C07C 209/00
[52] U.S. Cl. ....................... 564/405; 564/404
[58] Field of Search ........... 564/405, 404, 434, 443

[56] References Cited

U.S. PATENT DOCUMENTS

| | | | |
|---|---|---|---|
| 2,286,678 | 6/1942 | Gubelmann | 260/574 |
| 3,668,254 | 6/1972 | D'Amico et al. | 260/576 |
| 3,819,708 | 6/1974 | Manning et al. | 260/573 |
| 3,937,736 | 2/1976 | Freed et al. | 568/327 |
| 4,069,038 | 1/1978 | Teach | 71/95 |
| 4,110,105 | 8/1978 | Teach | 71/95 |
| 4,701,560 | 10/1987 | Regimbeau et al. | 564/404 |

FOREIGN PATENT DOCUMENTS 2305434  3/1976  France .

Primary Examiner—Allen J. Robinson
Assistant Examiner—Shailendra Kumar
Attorney, Agent, or Firm—Finnegan, Henderson, Farabow, Garrett and Dunner

[57] ABSTRACT

A process for the preparation of N-monoalkyl or N-monoalkenyl anilines wherein the aniline is contacted with an alkyl or alkenyl halide in the presence of a non-quaternizable organic base and a salt of a non-quaternizable organic base.

32 Claims, No Drawings

PROCESS FOR THE PREPARATION OF N-MONOALKYL OR N-MONOALKENYL ANILINES

The present invention relates to a process for the preparation of N-monoalkyl or N-monoalkenyl anilines. It more particularly relates to the preparation of N-monoallyl anilines.

The preparation of N-monoallyl anilines is particularly important in the case of trifluoromethyl aniline, because the monoallyl derivative obtained is an important intermediate in the synthesis of the herbicide N-meta-trifluoromethyl-1-phenyl-3-chloro-4-chloro-methyl-2-pyrrolidone, as described in French Pat. No. 2,305,434. However, according to this patent, the preparation of the N-monoallyl-meta-trifluoromethyl aniline intermediate requires allylating a trifluoromethyl aniline in which one of the hydrogen atoms is protected by an acetyl group, in order to prevent the formation of secondary diallylation products which cannot be utilized. Consequently, the process disclosed in this patent takes place in four stages: (1) protection of the amine by acetylation, (2) substitution of the remaining hydrogen by a metal; (3) condensation with an allyl halide; and (4) deacetylation.

However, since multi-stage processes are typically more difficult to implement and less economically advantageous than a single-stage process, the industry has long sought an economical single-stage process for the production of N-monoallyl-metatrifluoromethyl aniline. Additionally, since meta-trifluoromethyl aniline is a very valuable compound and is desirably conserved, a process is sought which provides high yields with respect to the meta-trifluoromethyl aniline starting material used.

One solution to this problem is disclosed in U.S. Pat. No. 4,701,560, which describes a single-step process for the allylation of meta-trifluoromethyl aniline comprising reacting an allyl halide, in an aqueous medium, with a substituted or unsubstituted meta-trifluoromethyl aniline, in the presence of (1) an alkali metal carbonate, an alkali metal hydrogen carbonate or an alkali metal hydroxide, and (2) a catalytic quantity of a tertiary amine. However, in order to produce only small quantities of secondary diallyl products by this method, it is necessary to limit the degree of conversion of the metatrifluoromethyl aniline by carrying out the reaction in the presence of less than a stoichiometric amount of the allyl halide. For example, the preferred ratio of meta-trifluoromethyl-aniline to allyl halide is reported to be about 2. Moreover, the yield of the N-monoallylaniline derivative produced, with respect to the meta-trifluoromethyl aniline introduced into the reactor, does not exceed about 40%, which is typically inadequate to obtain good economic profitability from the process.

Allylation reactions on anilines other than metatrifluoromethyl aniline are described, for example, in U.S. Pat. No. 2,286,678, which generally discloses the allylation of ortho- and para-hydroxyaniline by reaction with an alkenyl halide in the presence of a base as an acid acceptor. More specifically, this reference describes the allylation of para-hydroxyaniline in a medium constituted by an alcohol and in the presence of carbonate as the neutralizing agent. However, the N-monoallylhydroxyaniline yields obtained do not exceed those of the aforementioned patent, and also, non-negligible quantities of the diallyl derivative are undesirably formed. Thus, this method does not provide an economical process for obtaining the monoallyl derivative, as desired.

Additionally, U.S. Pat. No. 3,668,254 describes a process consisting of allylating 4-aminodiphenylamine with a polyhalopropene such as 2,3-dichloropropene in the presence of an acid acceptor such a triethylamine. As in the previous two cases, the yields obtained do not exceed 40%. Moreover, the triethylamine is used in a superstoichiometric quantity as compared with the allyl halide. From an economic standpoint, this method is very uninteresting, because the yields are too low and the cost of the starting materials used is too high.

Moreover, U.S. Pat. No. 3,819,708 describes the alkylation of paraphenylene diamines in various solvents in the presence of a tertiary amine such as triethylamine or a mineral base such as an alkali metal carbonate as the neutralizing agent of the hydrazide formed. The alkylating agents described are much less reactive than allyl halides and consequently the dialkylation problem is probably much less significant. However, the selectivity for the monoalkyl derivative, i.e., the yield of monoalkyl product compared with the dialkyl derivatives, is not described Despite the existence of a large amount of literature describing the alkylation or allylation of various anilines, as far as applicants are aware, no process has been described in the literature which provides both a high transformation rate of the starting aniline and, a high selectivity for the monosubstituted aniline as compared to the disubstituted aniline.

The process of the present invention overcomes the deficiencies in the prior art processes above by providing a single-step allylation process that can have both a high degree of conversion of the starting aniline and a high selectivity in favor of the monosubstituted aniline derivative.

The alkylation/alkenylation process of the present invention provides a process for the preparation of N-monoalkyl or N-monoalkenyl anilines, comprising the step of contacting an aniline and an alkyl or alkenyl halide in the presence of a non-quaternizable organic base and a salt of a non-quaternizable organic base prepared extrinsically or in situ.

The salt of the non-quaternizable organic base is preferably a non-quaternizable amine salt. It can be prepared by contacting within the reaction medium, or beforehand, a non-quaternizable amine, which is the same as or different from that used as the non-quaternizable organic base in the reaction medium, and an acid selected from halo, sulphuric, nitric, trifluoroacetic, perchloric, trifluoromethane-sulphonic and phosphoric acids. Among these acids, preference is given to halo acids such as hydrochloric or hydrobromic acid.

The alkyl or alkenyl halides are preferably chosen from compounds containing straight or branched chains of from 1 to 6 carbon atoms and which can also have at least one substituent selected from halogen atoms and aryl, aralkyl, halogenoaryl and nitroaryl radicals. Preferred halides are chlorides and bromides and more particularly the less expensive chlorides.

Preferred alkenyl halides are selected from allyl chloride, allyl bromide, crotyl chloride and 1-chloro-2-butene. Among these alkenyl halides, the present invention is more particularly directed at allyl halides, and more especially allyl chlorides.

Preferred alkyl halides are selected from isopropyl bromide, benzyl chloride and benzyl bromide.

The process according to the present invention is applicable to all anilines. However, it is of particular interest to slightly basic anilines, i.e., those having a pKa below 4.5. The preferred anilines are those having a pKa below 4.5 and which are represented by the following formula (I):

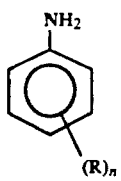

in which R stands for a halogen, a nitro group or an $A-C_n-X_{2n+1}$ group, in which X represents a halogen, A represents a covalent bond, an oxygen atom or a sulfur atom, and n is equal to 0, 1 or 2.

Suitable anilines of formula (I) include aniline, chloroanilines, fluoroanilines, nitroanilines, trihalogenomethyl anilines, trihalogenomethoxy anilines and trihalogenomethyl thio anilines.

The term non-quaternizable organic base encompasses all tertiary amines having at least one branched alkyl chain and preferably at least two branched alkyl chains. Examples of these amines are diisopropyl allyl amine, diisopropyl ethyl amine, triisopropyl amine, dicyclohexyl ethyl amine, diisobutyl allyl amine and diisopropyl propyl amine. Among these, preference is given to the use of diisopropyl ethyl amine.

Moreover, since the chosen acid for preparing the salt of the non-quaternizable organic base is preferably hydrochloric acid or hydrobromic acid, preference is given to the use of diisopropyl ethyl amine hydrochloride or hydrobromide as the salt of the non-quaternizable organic base.

The alkylation/alkenylation reaction is preferably carried out in the absence of a solvent other than the reagents, since the non-quaternizable base can serve as the solvent.

For better performance, preference is given to the use of a roughly stoichiometric quantity of alkyl or alkenyl halide compared with the aniline.

When the salt of the non-quaternizable organic base is formed in situ, the acid is preferably used in an approximately catalytic quantity, i.e., in a molar ratio based on the aniline of between 0.05:1 and 0.2:1.

When the non-quaternizable organic base does not serve as a solvent, it is used in an approximately stoichiometric quantity based on the alkyl or alkenyl halide. It is advantageously used in a molar ratio relative to the alkyl or alkenyl halide of between 1:1 and 1.5:1.

The reaction temperature advantageously ranges from 0 to 150° C; and will vary as a function of the reagents used and in particular, as a function of the pKa of the aniline and according to the nature of the halide. The reaction pressure is preferably atmospheric pressure. Typically, the reaction lasts between one and a few hours.

The present invention is further described in greater detail by the following non-limiting examples.

EXAMPLE 1

Into a 30 ml reactor and under magnetic stirring were introduced 0.497 ml (644.4 mg) or 4 mmoles of meta-trifluoromethyl aniline, 0.326 ml (306 mg) or 4 mmoles of allyl chloride, 0.697 ml (517 mg) or 4 mmoles of diisopropyl ethyl amine and 66.3 mg or 0.4 mmoles of diisopropyl ethyl amine hydrochloride.

The mixture was heated for 4 hours at 80° C. This was followed by the addition of 0.7 ml or 10N 30% NaOH and 20 ml of distilled water. The organic reagents and products were then extracted with diisopropyl ether and titrated by gas chromatography. The results of this titration are shown below in Table I.

A comparative test (C1) was carried out under the same conditions, but in the absence of diisopropyl ethyl amine hydrochloride.

TABLE I

| Examples | mTFMA | N-allyl mTFMA | N,N-diallyl mTFMA |
|---|---|---|---|
| 1 | 0.96 mmole | 2.60 mmole | 0.39 mmole |
| C1 | 2.11 mmole | 1.53 mmole | 0.13 mmole |

EXAMPLE 2

Example 1 and Comparative Test 1 were repeated, but the reaction time was limited to 2 hours.

The results are shown below in Table II.

TABLE II

| Examples | mTFMA | N-allyl mTFMA | N,N-diallyl mTFMA |
|---|---|---|---|
| 2 | 2.12 mmole | 1.57 mmole | 0.11 mmole |
| C2 | 3.52 mmole | 0.38 mmole | |

EXAMPLES 3-6

Example 2 was repeated (reaction time 2 hours at 80° C.), while varying the quantity of the diisopropyl ethyl amine salt or by only adding a halo acid. The reagent used and the result of these tests are shown below in Table III.

TABLE III

| Examples | Nature of the DIPEA salt or acid | mole acid (salt)/ mole mTFMA | mTFMA mmole | N-allyl mTFMA mmole | Diallyl mTFMA mmole |
|---|---|---|---|---|---|
| 3 | DIPEA/HCl | 4.7% | 2.78 | 1.08 | 0.06 |
| 4 | DIPEA/HCl | 15% | 2.03 | 1.61 | 0.13 |
| 5 | HCl (37%) in water | 10.2% | 2.19 | 1.52 | 0.12 |
| 6 | HBr (47%) in water | 9.9% | 1.52 | 1.96 | 0.22 |

EXAMPLE 7

Into a reactor were introduced 3.25 moles (523.6 g) of meta-trifluoromethyl aniline, 3.25 moles (420.1 g) of diisopropyl ethyl amine and 2.925 moles (223.8 g) of allyl chloride, the reactor being kept at 80° C. The allyl chloride was added slowly over a 2 hour period and, thereafter, the reactor was maintained at 80° C. for an additional 2 hour period.

| | Chloride pouring | | | | Maintained | | | |
|---|---|---|---|---|---|---|---|---|
| | 30 mn | 1h00 | 1h30 | 2h00 | 30 mn | 1h00 | 1h30 | 2h00 |
| TT %[1] allyl chloride | | | 1.2 | | 26.2 | 44.7 | 66.1 | 76.4 |

|  | Chloride pouring | | | | Maintained | | | |
| --- | --- | --- | --- | --- | --- | --- | --- | --- |
|  | 30 mn | 1h00 | 1h30 | 2h00 | 30 mn | 1h00 | 1h30 | 2h00 |
| TT % m.TFMA | 2.7 | 4.4 | 5.9 | 15.9 | 23.7 | 38.8 | 52.5 | 60.3 |
| RR %[2] N-allyl | 0.8 | 2.2 | 5.0 | 10.5 | 21.7 | 36.4 | 47.6 | 54.6 |
| RR % diallyl | 0 | 0 | 0.07 | 0.4 | 1.0 | 2.4 | 4.0 | 5.0 |
| Selectivity % | 100 | 100 | 98.8 | 96.6 | 95.4 | 93.9 | 92.3 | 91.7 |

[1] TT = rate of conversion = Reactant converted / Reactant introduced

[2] RR = yield = Desired product / Reactant introduced

The same test was carried out with the addition of 53.9 g (0.325 moles) of diisopropyl amine hydrochloride.

|  | Chloride pouring | | | | Maintained | | | |
| --- | --- | --- | --- | --- | --- | --- | --- | --- |
|  | 30mn | 1h00 | 1h30 | 2h00 | 30mn | 1h00 | 1h30 | 2h00 |
| TT % allyl chloride |  | 19.2 | 24.0 | 50.1 | 67.6 | 77.0 | 85.4 | 89.1 |
| TT % m.TFMA | 7.6 | 10.9 | 24.6 | 40.0 | 53.7 | 63.6 | 68.0 | 70.8 |
| RR % N-allyl | 2.2 | 8.6 | 19.5 | 36.6 | 49.3 | 55.8 | 61.0 | 64.0 |
| RR % diallyl | 0 | 0.1 | 0.6 | 2.0 | 3.7 | 5.1 | 6.1 | 6.8 |
| Selectivity % | 100 | 98.2 | 96.9 | 94.8 | 93.0 | 91.6 | 90.9 | 90.4 |

What is claimed is:

1. A process for the preparation of N-mono-alkenyl anilines, comprising the step of contacting an aniline with an alkenyl halide in the presence of a non-quaternizable tertiaryamine and a salt of a non-quaternizable tertiaryamine.

2. A process according to claim 1, wherein said aniline has a pKa below 4.5 and is represented by the formula

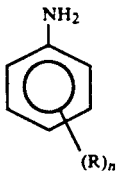

wherein:
R is a halogen, a nitro group or a group or a A-$C_n$-$X_{2n+1}$ group
wherein:
X is a halogen,
A is a covalent bond, an oxygen atom or a sulfur atom, and
n is 0, 1 or 2.

3. A process according to claim 2, wherein said aniline is selected from aniline, chloroanilines, fluoroanilines, nitroanilines, trihalogenomethyl anilines, trihalogenomethoxy anilines and trihalogenomethyl thio anilines.

4. A process according to claim 3, wherein said aniline is meta-trifluoromethyl aniline.

5. A process according to claim 1, wherein said alkenyl halide contains a straight or branched chain of from 1 to 6 carbon atoms which may bear substituents selected from halogen atoms and hydrocarbyl aryl, hydrocarbyl aralkyl, hydrocarbyl halogenoar and hydrocarbyl nitroaryl radicals.

6. A process according to claim 5, wherein said alkenyl halide is selected from allyl chloride, allyl bromide, crotyl chloride and 1-chloro- 2-butene.

7. A process according to claim 6, wherein said alkenyl halide is selected from allyl chloride and allyl bromide.

8. A process according to claim 1, wherein said non-quaternizable tertiary amine is selected from diisopropyl allyl amine, diisopropyl ethyl amine, triisopropyl amine, dicyclohexyl ethyl amine, diisobutyl allyl amine and diisopropyl propyl amine.

9. A process according to claim 1, wherein said salt of a non-quarternizable tertiary amine is obtained by contacting a non-quaternizable tertiary amine with an acid selected from halo acids, sulphuric acid, nitric acid, trifluoroacetic acid, perchloric acid, trifluoromethane-sulphonic acid and phosphoric acid.

10. A process according to claim 1, wherein said non-quaternizable tertiary amine is selected from diisopropyl allyl amine, diisopropyl ethyl amine, triisopropyl amine, dicyclohexyl ethyl amine, diisobutyl allyl amine and diisopropyl propyl amine and said salt of a non-quaternizable tertiary amine is obtained by contacting a non-quarternizable tertiary amine selected from diisopropyl allyl amine, diisopropyl ethyl amine, triisopropyl amine, dicyclohexyl ethyl amine, diisobutyl allyl amine and diisopropyl propyl amine with an acid selected from halo acids, sulphuric acid, nitric acid, trifluoroacetic acid, perchloric acid, trifluoromethane-sulphonic acid and phosphoric acid.

11. A process according to claim 10, wherein said salt of a non-quaternizable tertiary amine is obtained by contacting said non-quaternizable tertiary amine with said acid.

12. A process according to claim 11, wherein said acid is selected from the group consisting of hydrochloric and hydrobromic acid.

13. A process according to claim 12, wherein said non-quaternizable tertiary amine is diisopropyl ethyl amine.

14. A process according to claim 1, wherein the molar ratio of the alkenyl halide to aniline ranges from 0.9:1 to 1.2:1.

15. A process according to claim 1, wherein the molar ratio of said non-quaternizable tertiary amine to said alkenyl halide ranges from 1:1 to 1.5:1.

16. A process according to claim 11, wherein the molar ratio of said acid to said aniline ranges from 0.05:1 and 0.20:1.

17. A process for the preparation of N-mono-allyl metatrifluoromethyl aniline comprising contacting meta-trifluoromethyl aniline with an alkenyl halide selected from the group consisting of allyl chloride and allyl bromide, in the presence of diisopropyl ethyl amine and a salt selected from the group consisting of diisopropyl ethyl amine hydrochloride and diisopropyl ethyl amine hydrobromide.

18. A process for the preparation of N-mono-alkyl anilines, comprising contacting an aniline with an alkyl halide in the presence of a non-quaternizable tertiary amine and a salt of a non-quaternizable tertiary amine.

19. A process according to claim 18, wherein said aniline has a pKa below 4.5 and is represented by the formula

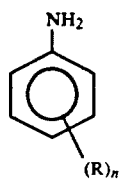

wherein:
R is a halogen, a nitro group or $A\text{-}C_n\text{-}X_{2n+1}$ group wherein:
X is a halogen,
A is a covalent bond, an oxygen atom or a sulfur atom, and
n is 0, 1 or 2.

20. A process according to claim 19, wherein said aniline is selected from aniline, fluoroanilines, nitroanilines, trihalogenomethyl anilines, trihalogenomethoxy anilines and trihalogenomethyl thio anilines.

21. A process according to claim 20, wherein said aniline is meta-trifluoromethyl aniline.

22. A process according to claim 18, wherein said alkyl halide contains a straight or branched chain of from 1 to 6 carbon atoms which may bear substituents selected from halogen atoms and hydrocarbyl aryl, hydrocarbyl aralkyl, hydrocarbyl halogenoaryl and hydrocarbyl nitroaryl radicals.

23. A process according to claim 22, wherein said alkyl halide is selected from the group consisting of isopropyl bromide, benzyl chloride and benzyl bromide.

24. A process according to claim 18, wherein said non-quaternizable tertiary amine is selected from diisopropyl allyl amine, diisopropyl ethyl amine, triisopropyl amine, dicyclohexyl ethyl amino, diisobutyl allyl amine and diisopropyl propyl amine.

25. A process according to claim 18, wherein said salt of a non-quaternizable tertiary amine is obtained by contacting a non-quaternizable tertiary amine with an acid selected from halo acids, sulphuric acid, nitric acid, trifluoroacetic acid, perchloric acid, trifluoromethanesulphonic acid and phosphoric acid.

26. A process according to claim 18, wherein said non-quaternizable tertiary amine is selected from diisopropyl allyl amine, diisopropyl ethyl amine, triisopropyl amine, dicyclohexyl ethyl amino, diisobutyl allyl amine and diisopropyl propyl amine and said salt of a non-quaternizable tertiary amine is obtained by contacting a non-quaternizable tertiary amine selected from diisopropyl allyl amine, diisopropyl ethyl amine, triisopropyl amine, dicyclohexyl ethyl amino, diisobutyl allyl amine and diisopropyl propyl amine with an acid selected from halo acids, sulphuric acid, nitric acid, trifluoroacetic acid, perchloric acid, trifluoromethane-sulphonic acid and phosphoric acid.

27. A process according to claim 26, wherein said salt of a non-quaternizable tertiary amine is obtained by contacting said non-quaternizable tertiary amine with said acid.

28. A process according to claim 27, wherein said acid is selected from the group consisting of hydrochlyoric and hydrobromic acid.

29. A process according to claim 28, wherein said non-quaternizable tertiary amine is diisopropyl ethyl amine.

30. A process according to claim 18, wherein the molar ratio of the alkenyl halide to aniline ranges from 0.9:1 to 1.2:1.

31. A process according to claim 18, wherein the molar ratio of said non-quaternizable tertiary amine to said alkenyl halide ranges from 1:1 and 1.5:1.

32. A process according to claim 27, wherein said molar ratio of said acid to said aniline ranges from 0.05:1 to 0.20:1.

* * * * *

UNITED STATES PATENT AND TRADEMARK OFFICE
CERTIFICATE OF CORRECTION

PATENT NO. : 5,132,460

DATED : JULY 21, 1992

INVENTOR(S) : JEAN-ROGER DESMURS ET AL.

It is certified that error appears in the above-identified patent and that said Letters Patent is hereby corrected as shown below:

Title Page, Title [54], change "M-MONOALKENYL" to --N-MONOALKENYL--.

Column 1, line 3, change "M-MONOALKENYL" to --N-MONOALKENYL--.

Claim 1, column 5, line 34, change "tertiaryamine" to --tertiary amine--; and
line 35, change "tertiaryamine" to --tertiary amine--.

Claim 2, column 5, line 49, delete "group or a" (second occurrence).

Claim 5, column 5, line 67, change "halogenoar" to --halogenoaryl--.

Claim 9, column 6, line 26, change "non-quarternizable" to --non-quaternizable--.

Claim 10, column 6, line 37, change "non-quarternizable" to --non-quaternizable--.

Claim 19, column 7, line 20, after "or" insert --a--.

Claim 20, column 7, line 27, after "aniline," insert --chloroanilines,--.

UNITED STATES PATENT AND TRADEMARK OFFICE
CERTIFICATE OF CORRECTION

PATENT NO. : 5,132,460

DATED : JULY 21, 1992

INVENTOR(S) : JEAN-ROGER DESMURS ET AL.

It is certified that error appears in the above-identified patent and that said Letters Patent is hereby corrected as shown below:

Claim 24, column 8, line 2, change "amino" to --amine--.

Claim 26, column 8, line 13, change "amino" to --amine--; and line 18, change "amino" to --amine--.

Claim 28, column 8, lines 29 and 30, change "hydrochlyoric" to --hydrochloric--.

Claim 30, column 8, line 35, change "alkenyl" to --alkyl--.

Claim 31, column 8, line 39, change "alkenyl" to --alkyl--.

Signed and Sealed this

Twenty-eighth Day of September, 1993

Attest:

BRUCE LEHMAN

*Attesting Officer*     *Commissioner of Patents and Trademarks*